United States Patent [19]

Clark, Jr. et al.

[11] 4,289,499
[45] Sep. 15, 1981

[54] SELECTING PERFLUOROCARBON COMPOUNDS FOR SYNTHETIC BLOOD

[75] Inventors: Leland C. Clark, Jr., Cincinnati, Ohio; Robert E. Moore, Wilmington, Del.

[73] Assignees: Childrens Hospital Medical Center, Philadelphia, Pa.; Suntech, Inc., Cincinnati, Ohio

[21] Appl. No.: 189,509

[22] Filed: Sep. 22, 1980

Related U.S. Application Data

[63] Continuation-in-part of Ser. No. 81,584, Oct. 3, 1979, abandoned, which is a continuation-in-part of Ser. No. 950,959, Oct. 13, 1978, abandoned.

[30] Foreign Application Priority Data

Oct. 12, 1979 [JP] Japan .................................. 54-130953

[51] Int. Cl.³ .......................................... A61K 31/02
[52] U.S. Cl. ............................... 23/230 B; 73/61.1 R; 424/352
[58] Field of Search ....................... 23/230 B; 424/352

[56] References Cited

U.S. PATENT DOCUMENTS

| | | | |
|---|---|---|---|
| 3,911,138 | 10/1975 | Clark, Jr. | 424/352 |
| 3,989,843 | 11/1976 | Chabert | 424/352 X |
| 4,105,798 | 8/1978 | Moore | 424/352 |

OTHER PUBLICATIONS

L. C. Clark, Jr. et al., Federation Proc., 34, 1468-1477 (1975).
R. P. Geyer, Federation Proc., 34, 1499-1505 (1975).

Primary Examiner—Sidney Marantz
Attorney, Agent, or Firm—J. Edward Hess; Donald R. Johnson

[57] ABSTRACT

A process for selecting a perfluorocarbon compound from those having about 9 to 12 carbon atoms for preparing synthetic blood compositions. The process involves determining the critical solution temperature of the perfluorocarbon compound in a solvent such as n-hexane. The perfluorocarbon compound is accepted as suitable for preparing a synthetic blood composition if its critical solution temperature falls below a selected temperature set by the number of carbon atoms in the perfluorocarbon compound.

5 Claims, 1 Drawing Figure

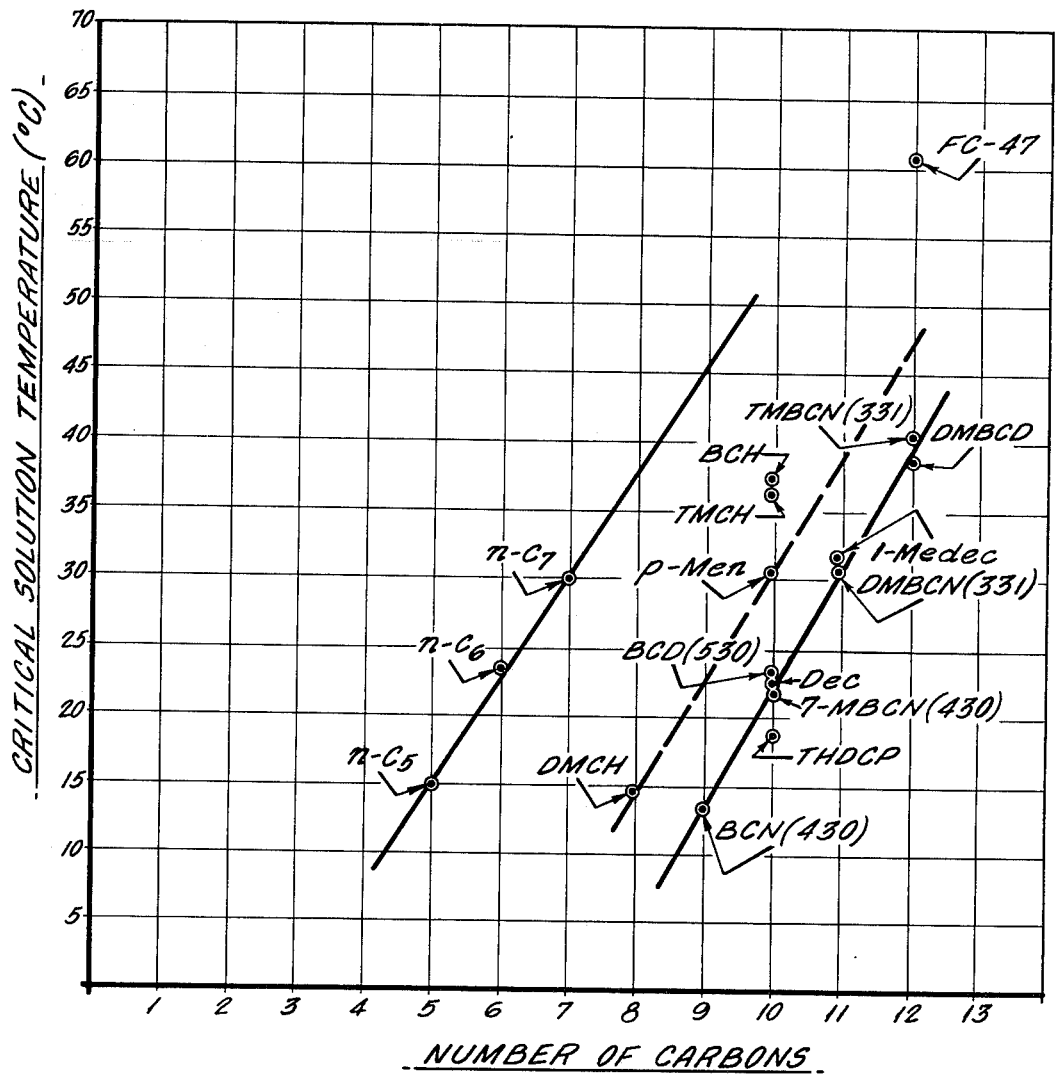

SELECTING PERFLUOROCARBON COMPOUNDS FOR SYNTHETIC BLOOD

CROSS-REFERENCE TO RELATED CASES

This application is a continuation-in-part of application Ser. No. 81,584, filed Oct. 3, 1979 in the name of Clark, Jr. et al, abandoned, which was a continuation-in-part of application Ser. No. 950,959, filed Oct. 13, 1978 in the name of Clark, Jr., et al., abandoned.

BACKGROUND OF THE INVENTION

This invention relates to a method for determining rates of transpiration of certain perfluorocarbons from the body of animals based on a particular physical property of said perfluorocarbons. More particularly, this invention relates to a process for selecting a perfluorocarbon useful as a synthetic blood component which comprises determining the critical solution temperature of said perfluorocarbon and selecting those perfluorocarbons having about 9 to 12 carbon atoms which have critical solution temperatures generally less than 20°–45° C. as further defined below.

The use of perfluorocarbons as synthetic blood components is known, for example, from U.S. Pat. No. 3,911,138 and U.S. Pat. No. 4,105,798. In these and other teachings, it is shown that certain classes of perfluorocarbons, in water emulsion forms, can be administered to animals as a synthetic blood because of the ability of the composition to carry oxygen and $CO_2$ through the body.

Examples of typical perfluorocarbons which have been tested for their ability to serve as synthetic blood components include perfluoro(1-methyldecalin); perfluoromethylcyclohexane; perfluoro(1,3-dimethylcyclohexane); perfluorodecalin; perfluorodimethyldecalin; perfluoroadamantane; perfluoromethyladamantane; perfluorodimethyladamantane; perfluoro-n-pentane; perfluorohexane; perfluoroheptane; perfluorobicyclo[4.3.0]nonane; perfluorotetrahydrodicyclopentadiene; perfluoro-7-methylbicyclo[4.3.0]nonane; perfluorobicyclo[5.3.0]decane; perfluoro-p-menthane; perfluorotetramethylcyclohexane; perfluoro-n-butylcyclohexane; perfluorotrimethylbicyclo[3.3.1]nonane; and the like. Of these, the cyclic perfluorocarbons are preferred.

Other perfluorocarbons useful as synthetic blood components include, in addition to the above, substituted perfluorocarbons such as other halogen substituted derivatives including mono- or di-bromo, iodo, etc., perfluorocarbons, specifically perfluorooctyl bromide. The presence of a bromine atom in place of a carbon atom is equivalent to the effect of two carbon atoms in vapor pressure. Other hetero perfluorocarbons include perfluoro cyclic amines, and perfluoro cyclic ethers, as well as mixtures of the same with the aforesaid perfluoro paraffinic or cyclic hydrocarbons. Therefore, the term "perfluorocarbon" as used herein is intended to include such diverse compounds and mixtures which may be selected according to the method of this invention.

These compounds and other like candidates, are tested for various properties to determine their suitability as synthetic blood components, including the ability of the body to excrete the perfluorocarbon within a suitable period of time (i.e., the transpiration rate), as shown in the abovementioned patents. These tests are normally determined by either injecting the pure perfluorocarbon into the abdominal cavity and measuring said rate, or by administering the perfluorocarbon in the form of an emulsion into the blood stream and then taking measurements.

As a result of these and other tests, it has been determined over a period of time that the most preferred perfluorocarbons are those having from 9 to 12 carbon atoms. Those compounds with less carbon atoms have too high a vapor pressure for the body to tolerate in that the material comes out of the body too fast and causes gas embolism, while those having too many carbon atoms tend not to have desirable oxygen solubilities, as well as having, in general, too long a residence time in body tissues. Generally speaking, however, each of these determinations has been arrived at empirically, with no known correlation between the physical structure and properties of the perfluorocarbon and its effectiveness as a synthetic blood component.

Although the most preferred perfluorocarbons are those having from 9 to 12 carbon atoms, the process of the invention can be used to screen candidates which have about 9 to 12 carbon atoms, including numbers of carbon atoms less than 8 or greater than 12. A compound having 8 carbon atoms for example might be useful as a component of a synthetic blood composition, in admixture with a compound having 9 to 12 carbon atoms. A person skilled in the art, in the light of the present specification, can with routine experimentation apply the process of the invention to perfluorocarbons generally as disclosed herein.

SUMMARY OF THE INVENTION

It has now been found, in accordance with the present invention, that when the critical solution temperature of a given perfluorocarbon is measured against the number of carbon atoms of said perfluorocarbon, that there is a definite correlation between said critical solution temperatures for any given carbon atom number and the transpiration rate of said perfluorocarbon in the animal, and that further those perfluorocarbons having critical solution temperatures greater than as defined herein possess transpiration rates which fall outside the range of said rates which may be safely used in animals. Thus, it is possible, on the basis of said critical solution temperatures, to select those candidate perfluorocarbons which fall inside the range and are most effective in preparing synthetic blood compositions.

DESCRIPTION OF THE DRAWING

FIG. 1 is a graph depicting the critical solution temperatures for a series of illustrative paraffinic and cyclic perfluorocarbons. In this drawing, the abbreviations correspond to those compounds listed in Table I below with the abbreviations designated in parenthesis.

The dotted line defines the upper limit of critical solution temperature for those perfluorocarbons of a given carbon atom number which are useful as synthetic blood components. In other words, any perfluorocarbon falling below and to the right of the dotted line is defined as one useful as a synthetic blood component.

DESCRIPTION OF THE INVENTION

The critical solution temperature of the perfluorocarbons may readily be determined by dissolving the same in an equal volume of n-hexane, and then lowering the temperature of the solution slowly until the solution becomes milky, which is defined as the critical solution temperature.

It should be understood that while n-hexane is preferred, any suitable solvent may be employed in its place such as, for example, n-heptane, benzene, carbon tetrachloride, water, or the like.

The following procedure was employed to determine the critical solution temperature for a series of perfluorocarbons. The results of these determinations are set forth in Table I below:

Procedure:

Equal volumes of fluorocarbons and n-hexane are added to a test tube and heated until the two layers become completely miscible. The solution is then cooled at a rate of ~0.2° C./min. The solution is stirred manually with a calibrated thermometer graduated in 0.1° C. The temperature at which the solution becomes milky is the critical solution temperature.

TABLE I

Critical Solution Temperature (°C.) in n-Hexane

| Perfluorocarbon | °C. | Abbreviation |
|---|---|---|
| F-n-pentane | 14.7 | n-C$_5$ |
| F-hexane | 23.0 | n-C$_6$ |
| F-heptane | 29.0 | n-C$_7$ |
| F-dimethylcyclohexane | 13.0 | DMCH |
| F-bicyclo[4.3.0]nonane | 12.8 | BCN(430) |
| F-tetrahydrodicyclopentadiene | 18.2 | THDCP |
| F-7-methylbicyclo[4.3.0]nonane | 21.5 | 7-MBCN(430) |
| F-decalin | 22.0 | DEC |
| F-bicyclo[5.3.0]decane | 22.5 | BCD(530) |
| F-p-menthane | 30.2 | p-MEN |
| F-tetramethylcyclohexane | 36.5 | TMCH |
| F-n-butylcyclohexane | 36.6 | BCH |
| F-1-methyldecalin | 31.0 | 1-Medec |
| F-trimethylbicyclo[3.3.1]nonane | 40.2 | TMBCN(331) |
| F-dimethylbicyclo[3.3.1]nonane | 30.4 | DMBCN(331) |
| F-dimethylbicyclo[5.3.0]decane | 38.2 | DMBCD |
| F-tributylamine(FC-47) | 60.6 | FC-47 |

As disclosed in the above-cited U.S. patents, transpiration rate is determined by injecting the neat perfluorocarbon into the abdominal cavity of the animal and measuring by known techniques the rate at which the material is excreted by the animal over a series of about 10–150 days.

The transpiration rate for a selected series of perfluorocarbons was measured in mice by these methods, with the following results:

TABLE II

Transpiration Rates of Fluorocarbons (nanograms/min.)

| Fluorocarbon | DAY | | | | | | | | | |
|---|---|---|---|---|---|---|---|---|---|---|
| | 1 | 3 | 4 | 10 | 20 | 35 | 50 | 75 | 100 | 125 |
| bicyclo[4.3.0]nonane | — | — | — | 1315 | 1500 | 1775 | 1450 | 1060 | 400 | — |
| exo + endo THDCP | 1048 | 1104 | 1285 | — | — | 1000 | 850 | 600 | 300 | — |
| 7-methylbicyclo[4.3.0]nonane | — | — | — | 430 | 980 | 925 | 850 | 790 | 480 | — |
| decalin | 280 | — | 500 | 560 | 640 | 700 | 750 | 710 | 600 | 470 |
| bicyclo[5.3.0]decane | 650 | — | 885 | — | — | — | — | — | — | — |
| p-menthane | — | 150 | — | 200 | 230 | 250 | 250 | 200 | — | — |
| n-butylcyclohexane | 50 | 50 | — | 100 | 100 | 110 | — | — | — | — |
| 1-medecalin | — | 100 | — | 110 | 150 | 250 | 250 | 250 | 250 | — |
| trimethylbicyclo[3.3.1]nonane | — | 200 | — | 350 | 500 | 600 | 700 | 800 | 700 | 250 |

When these data are compared with the critical solution temperatures of these same perfluorocarbons in Table I, it will be seen that a correlation exists between the critical solution temperature and the transpiration rate of a series of fluorocarbons of the same carbon number, i.e., the lower the C.S.T., the faster the material is transpired from mice.

Thus, since lower residence time in body tissues is desirable, it is possible from this known correlation to determine from critical solution temperature data which perfluorocarbons will have a satisfactory transpiration rate without having to perform the actual, arduous, time-consuming transpiration rate tests.

From the above data, and as shown on the graph of FIG. 1, it has been determined that when said data are correlated against the known transpiration rates of said perfluorocarbons for any given carbon atom number, the upper limits of the critical solution temperatures within which a perfluorocarbon having satisfactory transpiration rates may be chosen are as follows:

| Carbon Atoms | C.S.T. (°C.) |
|---|---|
| C$_9$ | less than 20 |
| C$_{10}$ | less than 30 |
| C$_{11}$ | less than 35 |
| C$_{12}$ | less than 45 |

It will thus be evident that all paraffinic compounds are outside the desired range, and that as the paraffinic side chain on cyclic materials is increased, these compounds likewise tend to fall outside of said range. Conversely, the more compact and dense the perfluorocarbon structure is, the faster it is released from the animal.

The invention claimed is:

1. A process for selecting perfluorocarbon compounds from those having from about 9 to 12 carbon atoms for preparing synthetic blood compositions comprising:
   (a) dissolving a candidate perfluorocarbon compound in a solvent;
   (b) determining the critical solution temperature of said candidate perfluorocarbon; and
   (c) accepting the candidate perfluorocarbon compound for preparing a synthetic blood composition when said candidate compound has a critical solution temperature of less than;
      (1) a first temperature when the perfluorocarbon has nine carbon atoms;
      (2) a second temperature when the perfluorocarbon has ten carbon atoms;
      (3) a third temperature when the perfluorocarbon has eleven carbon atoms;
      (4) a fourth temperature when the perfluorocarbon has twelve atoms; and
   whereby the accepted perfluorocarbon compound has a transpiration rate in animals falling within a predetermined range.

2. The process of claim 1 wherein the candidate perfluorocarbon is a cyclic perfluorocarbon.

3. The process of claim 1 wherein the candidate perfluorocarbon is a paraffinic fluorocarbon.

4. A process for selecting perfluorocarbon compounds from those having from about 9 to 12 carbon atoms for preparing synthetic blood compositions comprising:

(a) dissolving a candidate perfluorocarbon compound in n-hexane;

(b) determining the critical solution temperature of said candidate perfluorocarbon; and (c) accepting the candidate perfluorocarbon compound for preparing a synthetic blood composition when said candidate compound has a critical solution temperature of less than:

(1) 20° C. when the perfluorocarbon has nine carbon atoms;

(2) 30° C. when the perfluorocarbon has ten carbon atoms;

(3) 35° C. when the perfluorocarbon has eleven carbon atoms;

(4) 45° C. when the perfluorocarbon has twelve carbon atoms; and whereby the accepted perfluorocarbon compound has a transpiration rate in animals falling within a predetermined range.

5. The process of claim 4 wherein the candidate perfluorocarbon is a cyclic perfluorocarbon.

* * * * *